US008500651B2

(12) United States Patent
Eriksen et al.

(10) Patent No.: US 8,500,651 B2
(45) Date of Patent: Aug. 6, 2013

(54) VOLUMETRIC PHYSIOLOGICAL MEASURING SYSTEM AND METHOD

(75) Inventors: Morten Eriksen, Oslo (NO); Erik Eriksen, Bekkestua (NO)

(73) Assignee: Volusense AS, Bergen (NO)

( * ) Notice: Subject to any disclaimer, the term of this patent is extended or adjusted under 35 U.S.C. 154(b) by 1401 days.

(21) Appl. No.: 12/112,572

(22) Filed: Apr. 30, 2008

(65) Prior Publication Data
US 2008/0270067 A1    Oct. 30, 2008

Related U.S. Application Data

(60) Continuation of application No. 10/671,011, filed on Sep. 25, 2003, now Pat. No. 7,390,307, which is a continuation-in-part of application No. 10/087,302, filed on Feb. 28, 2002, now Pat. No. 6,945,941, which is a division of application No. 09/428,358, filed on Oct. 28, 1999, now Pat. No. 6,374,667.

(51) Int. Cl.
| | |
|---|---|
| *A61B 5/103* | (2006.01) |
| *A61B 5/117* | (2006.01) |
| *A61B 5/08* | (2006.01) |
| *G01F 1/56* | (2006.01) |
| *G01F 1/716* | (2006.01) |
| *G01F 1/58* | (2006.01) |
| *G01P 5/08* | (2006.01) |
| *G01R 33/02* | (2006.01) |
| *G01R 33/00* | (2006.01) |
| *G01R 33/12* | (2006.01) |
| *G01N 27/72* | (2006.01) |

(52) U.S. Cl.
USPC ...... 600/534; 600/595; 73/861.08; 73/861.15; 324/258; 324/262; 324/228

(58) Field of Classification Search
USPC ............... 600/529–543, 595, 587; 73/861.08, 73/861.11, 861.12, 861.13, 861.15; 324/228, 324/262, 258
See application file for complete search history.

(56) References Cited

U.S. PATENT DOCUMENTS

| | | | |
|---|---|---|---|
| 2,649,573 A | 8/1953 | Goldberg | |
| 2,843,825 A | 7/1958 | Lush | |
| 3,142,796 A | 7/1964 | Goldberg | |
| 3,547,106 A * | 12/1970 | Bornmann | 600/534 |
| 3,560,845 A | 2/1971 | Goldberg | |
| 3,658,052 A * | 4/1972 | Alter | 600/534 |

(Continued)

FOREIGN PATENT DOCUMENTS

| | | |
|---|---|---|
| DE | 4215901 | 8/1993 |
| FR | 2821262 | 8/2002 |

(Continued)

OTHER PUBLICATIONS

Partial International Search Report, dated Jun. 21, 2010 for corresponding PCT Application No. PCT/US2010/026286.

(Continued)

*Primary Examiner* — Navin Natnithithadha
(74) *Attorney, Agent, or Firm* — Mintz Levin Cohn Ferris Glovsky and Popeo, P.C.

(57) ABSTRACT

A system and method for measuring volumes and areas using electromagnetic induction techniques. A current is generated and fed into one of two coil assemblies to induce voltage into another coil assembly to provide accurate values for volume or area.

28 Claims, 9 Drawing Sheets

U.S. PATENT DOCUMENTS

| | | | |
|---|---|---|---|
| 3,731,184 A | | 5/1973 | Goldberg |
| 4,083,002 A | | 4/1978 | Allport |
| 4,258,718 A | | 3/1981 | Goldman |
| 4,308,872 A | | 1/1982 | Watson |
| 4,444,064 A | * | 4/1984 | Wolfinger ............ 73/862.326 |
| 4,652,823 A | | 3/1987 | Sutton |
| 4,694,837 A | | 9/1987 | Blakeley |
| 4,815,473 A | | 3/1989 | Watson et al. |
| 4,991,587 A | | 2/1991 | Blakeley |
| 5,038,785 A | | 8/1991 | Blakeley |
| 5,131,399 A | | 7/1992 | Sciarra |
| 5,394,882 A | | 3/1995 | Mawhinney |
| 5,738,102 A | | 4/1998 | Lemelson |
| 5,749,365 A | | 5/1998 | Magill |
| 5,825,293 A | | 10/1998 | Ahmed |
| 5,882,300 A | | 3/1999 | Malinouskas |
| 5,957,854 A | | 9/1999 | Besson |
| 5,961,720 A | * | 10/1999 | Imaeda et al. ............ 117/214 |
| 5,964,720 A | | 10/1999 | Pelz |
| 6,106,481 A | | 8/2000 | Cohen |
| 6,374,667 B1 | | 4/2002 | Eriksen |
| 6,434,411 B1 | | 8/2002 | Duret |
| 6,436,053 B1 | | 8/2002 | Knapp |
| 6,480,111 B2 | | 11/2002 | Canady |
| 6,740,046 B2 | | 5/2004 | Knapp |
| 6,783,498 B2 | | 8/2004 | Sackner et al. |
| 6,945,941 B2 | | 9/2005 | Eriksen |
| 2002/0032386 A1 | | 3/2002 | Sackner |
| 2002/0115925 A1 | | 8/2002 | Arvin |

FOREIGN PATENT DOCUMENTS

| | | |
|---|---|---|
| GB | 1596298 | 8/1981 |
| GB | 2116725 | 9/1983 |
| JP | 53126786 A2 | 11/1978 |
| WO | 9013259 | 11/1990 |
| WO | 0178577 | 10/2001 |

OTHER PUBLICATIONS

Office Action dated Aug. 4, 2006 for corresponding European Application No. 04787568.7.

Response to Office Action dated Dec. 1, 2006 for corresponding European Application No. 04787568.7.

Office Action dated Jan. 19, 2007 for corresponding European Application No. 04787568.7.

Response to Office Action dated Jul. 17, 2007 for corresponding European Application No. 04787568.7.

European Search Report, dated Mar. 9, 2009 for corresponding European Application No. 09152262.3.

Office Action dated Nov. 24, 2009 for corresponding European Application No. 09152262.3.

Response to Office Action dated May 21, 2010 for corresponding European Application No. 09152262.3.

English-language abstract for DE4215901.

TTI: "Products" Dec. 5, 2002, Tristan Technologies, Inc., HTTP://web.archive.org/web/20021205005908/HTTP://tristantech.com/prod_biomagnet.html, XP002332664, pp. 1-11.

Tavrin Y. et al: "A Second-Order SQUID Gradiometer Operating at 77 K", Superconductor Science and Technology, IOP Publishing, Techno House, Bristol, GB, vol. 7, No. 5, May 1, 1994, pp. 265-268, XP00574844.

Mosher J.C. et al.: "Fetal Magnetocardiography: Methods for Rapid Data Reduction", Review of Scientific Instruments, American Institute of Physics, NY, U.S., vol. 68, No. 3, Mar. 1997, pp. 1587-1595, XP000685079.

Ripka P., et al: "Fluxgate sensor for magnetopneumometry", Sensors and Actuators A, Elsevier Sequoia S.A., Lausanne, CH, vol. 60, No. 1-3, May 1997, pp. 76-79, XP004134599.

* cited by examiner

VOLUMETRIC PHYSIOLOGICAL MEASURING SYSTEM AND METHOD

CROSS-REFERENCE TO RELATED APPLICATIONS

This application is a continuation of U.S. patent application Ser. No. 10/671,011, filed Sep. 25, 2003, now U.S. Pat. No. 7,390,307, which is a continuation-in-part of U.S. Divisional patent application Ser. No. 10/087,302, filed Feb. 28, 2002, now U.S. Pat. No. 6,945,941, which in turn is a divisional application of U.S. patent application Ser. No. 09/428,358, filed Oct. 28, 1999, now U.S. Pat. No. 6,374,667, issued Apr. 23, 2002, which are incorporated herein by reference.

FIELD OF THE INVENTION

The invention relates to a system and method for accurate measurements of volume and area of objects, utilizing electromagnetic induction techniques.

BACKGROUND OF THE INVENTION

Numerous opportunities exist in which accurate measurements of volume and area are essential, particularly of objects or portions of objects having variable volumes or areas. For example, in the field of medicine, the recording of breathing volumes in patients is often quite critical. Unfortunately these measurements are often crude and inaccurate, or at best rely upon outmoded technical modalities or upon unreliable. The recording of breathing volumes in patients is currently either performed by connecting a volume flow-sensing device to a subject's airway (e.g. by use of a spirometer or tachymeter) or by measuring the mechanical excursions of the chest and abdominal walls. For long-term monitoring purposes, the airway-based techniques are inappropriate since they interfere with normal breathing and are unpleasant for the patient. This is particularly relevant to children and certain other patients. Although airway-based techniques are currently used in patients dependent on respiratory-assist devices there may be less intrusive and more reliable means of obtaining such data.

Similarly, techniques that rely on recordings of chest and abdominal wall movements are either strain gauge based (recording of changes in body circumference length), or based on elastic inductive electrical conductor loops arranged around the chest and abdomen of the patient. Recordings of the inductance of the loops can then be used to estimate the magnitude of cross sectional area variations of the chest and abdominal compartments. U.S. Pat. No. 4,308,872 is an example of this self-inductance loop estimation technology. Such methods might be used for quantitative measurements of respiratory volumes only after a calibration procedure where the patient breathes known air volumes with variable respiration movement distributions between the chest and abdominal compartments.

Currently, most devices for measurements of chest volume variations have shortcomings related to calibration, stability, accuracy or reliability. The methods are either based on measurements of circumference of the chest and abdomen (strain-gauge transducers), or on measurements of the electrical inductance of conductor loops arranged around the chest and abdomen. The reason for using abdominal sensors is that the downward movement of the diaphragm during inspiration causes volume changes of both the chest and abdomen that have to be added to estimate the lung volume excursions. There is no fixed ratio between the abdominal and chest volume variations. Indeed, the relative contributions to total volume variations might even vary as a consequence of respiratory effort, airway resistance or sleep state. Thus, independent calibrations of both measurement sites are necessary (when using known techniques) to estimate the actual volume variations caused by respiration.

The strain gauge or circumferential distance methods have no simple or reproducible relation between the measured variations and the volumes that are measured. This relation depends on assumptions about the relation between the area enclosed by the loop and the length of the loop that are valid only for a fixed geometry. Although some of the methods based on inductance may claim that area is measured (i.e., it is assumed to be proportional to loop inductance), the assumption is only valid as long as the relative shape of the loop is conserved. Unfortunately, this is not the case for the cross-sectional area variations of the human chest or abdomen that are caused by respiration.

Common to all area-based methods is a considerable uncertainty in the calculations of volume variations from the estimated area variations. One reason for this is that only point samples of the area (at the sites of the transducers) are measured. To relate area variations to volumes, some means of calibration is necessary. The calibration procedure depends highly upon patient cooperation to obtain coefficients for both chest and abdominal measurement sites, and is virtually inapplicable to small children, patients with dyspnea (shortness of breath), and unconscious patients.

This invention describes novel systems and methods for volume and area measurements, based on electrical inductance, in ways which eliminate the shortcomings discussed above. The invention does not depend on patient cooperation for calibration and is a true volume or area measurement method that does not depend on assumptions about the relations between circumference, area and volume.

SUMMARY OF THE INVENTION

A new family or class of devices is provided for recording of cross-sectional areas and volumes of objects, in particular portions of the human body. This includes static measurements as well as measurements of the smaller overlying variations in area and volume caused by respiratory and cardiac activity. The principle relies on measurement of electromagnetic induction between one or more electrical conductor loops wrapped around a body part to be measured, and one or more remotely located electromagnetic coil arrangements. By proper design of the coils, the induced voltages that are measured will be proportional to the area or volume that is measured.

In one embodiment, a device is provided for measuring the movement of an object which comprises means for creating time-varying magnetic fields at least large enough to surround the object. Electrical circuits are adapted to conform to the surface of the object, and voltage monitoring means are connected to the electrical circuits, whereby motion of the surface creates a measurable change in induced voltage in the circuits that correlates to the movement of the object.

In another embodiment, a method is provided for measuring the area or volume of an object which comprises the steps of adapting electrical circuits to conform to the object surface, and measuring the voltage induced in the circuits by a time-varying magnetic field surrounding the object, whereby the change in the area or volume of the object may be calculated without calibration of the device to the individual.

DETAILED DESCRIPTION OF THE INVENTION

Figure 1:
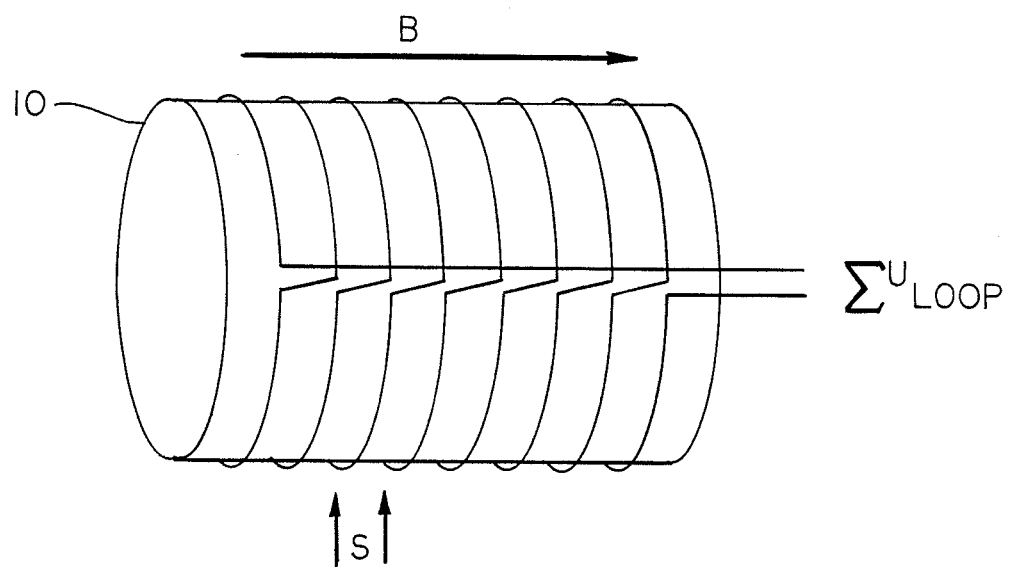
FIG. 1 is an arrangement of serially connected loops and a magnetic field vector.

By way of technical background, and in reference to FIG. 1, it may be seen that the induced voltage in a closed electrical conductor loop 10 perpendicular to a homogeneous magnetic field that varies with time is:

$$U_{loop} = (dB/dt) A_{loop} \quad \text{Eq. 1}$$

where B is the magnetic field strength, and $A_{loop}$ is the area of the loop regardless of its shape and t is time.

Thus, when a homogeneous magnetic field with a known intensity and temporal variation and with 1 direction that is along a patient's body axis is generated, measurements of induced voltages in conductor loops wrapped around the patient's body will give accurate area measurements. In order to measure volume, it is necessary to add together the volumes of a stack of slices, each with a measured area and a known thickness. This is readily accomplished by using several conductor loops wrapped around the patient's body. If the spacing between the loops is constant and known, then the volume to be measured ($V_{body}$) may be expressed as:
Eq. 2)

$$V_{body} = s \lim_{s \to 0} \sum A_{loop} = s(dt/dB) \lim_{s \to 0} \sum U_{loop}$$

where s is the spacing between the loops.

Summation of the induced voltages is accomplished by electrical serial connection of the loops, effectively reducing the complexity of the system, since only one voltage needs to be measured. This is an important advantage of the invention disclosed herein resulting in reduced system complexity. The choice of the loop spacing s (also referred interchangeably herein as distance d) is a compromise between accuracy and convenience in the design of the volume transducer. A low value of s means that a higher number of loops will be needed to encompass the measurement region, which typically is from the level of the axilla and down to the crest of the hips, when measuring a torso. If the number of loops becomes high, the self-inductance of the serially connected loops starts to increase dramatically, with implications for the design of the electronic circuits. A preferable embodiment is to use values of s in the range of four to eight cm, which are the smallest values to be used for infants. This typically results in eight (8) to ten (10) loops. Other configurations, however, are possible. The magnetic field need only be homogeneous within the volume occupied by the relevant parts of the patient's body or other object being measured. Practical experience indicates that a field of sufficient intensity and homogeneity can be generated just by arranging a conductor wire as a vertical rectangular loop, following the floor, walls and ceiling of the room, and feeding an alternating current through the loop. Preferable values are 10 kHz to 200 kHz with currents below 1 A, although other configurations are possible. For example, more than one electrical conductor loop may be used.

Figure 4:
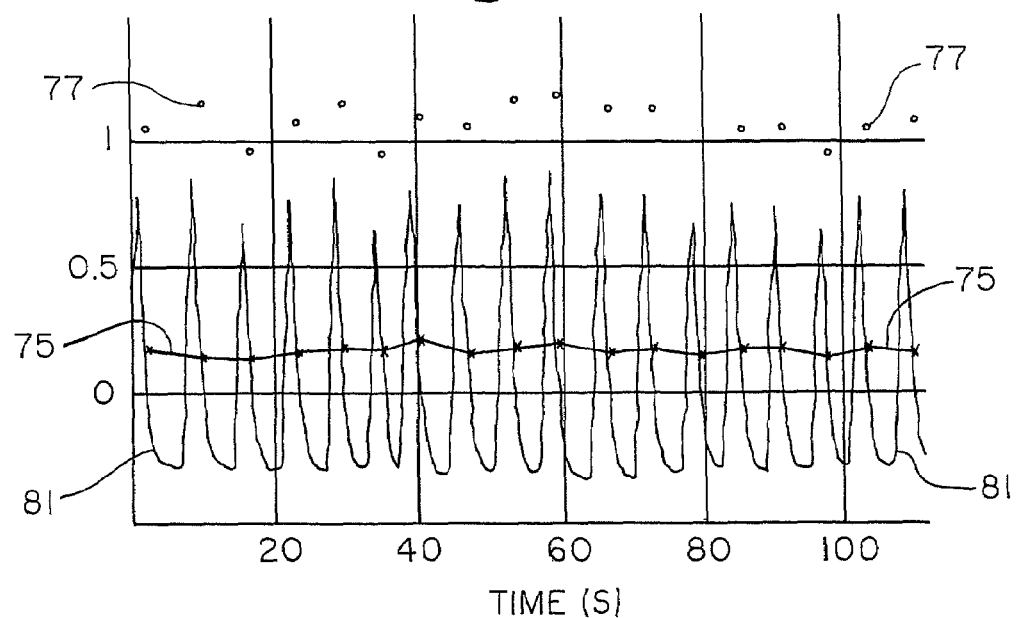
FIG. 4 is a sample recording from the use of the system of FIG. 2.
Figure 5:
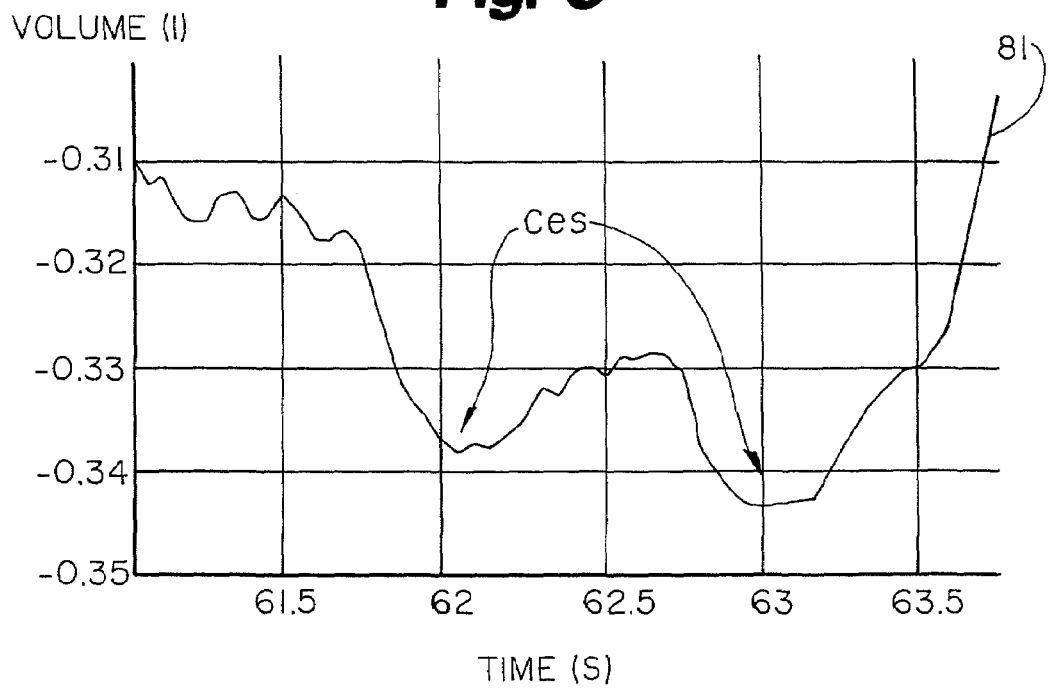
FIG. 5 is a magnified view of the raw volume curve of FIG. 4, demonstrating cardiac pulsations in volume.
Figure 6:
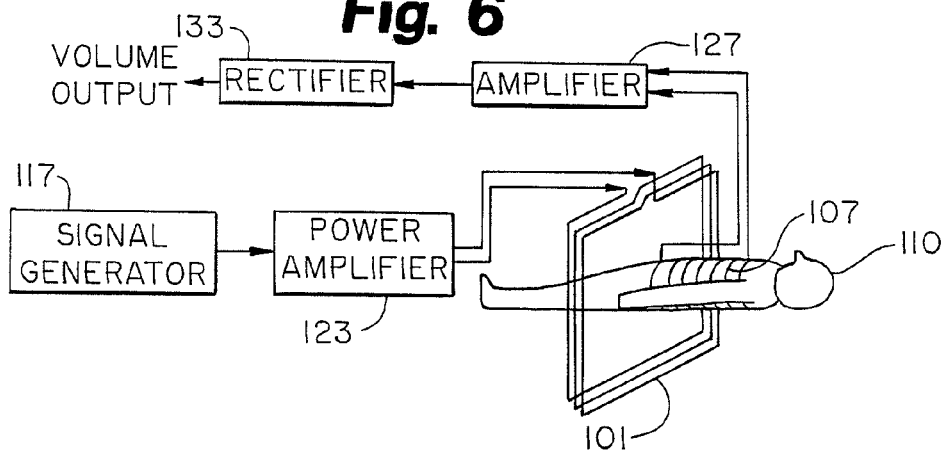
FIG. 6 is a schematic view of a second embodiment of the invention.

FIGS. 2-8 relate to a first embodiment of this invention discussed below. This embodiment, shown in block diagram form in FIG. 2, comprises integrating both the alternating current source for the current loop that generates the magnetic field and the circuits needed to amplify and rectify the returned signal into a single unit. Stable crystal oscillator 30 controls system 20, with the output frequency of the oscillator being divided down to the desired value by binary counter 34. The suggested values of 1 MHz and a division of 16 are arbitrary. It is, however, an advantage that the signal fed into the power amplifier 36 is a symmetric square wave, since this waveform lacks even frequency harmonics. The removal of unwanted harmonic frequency components by filter 37 is then easier. Such removal of harmonics is preferable to avoid radiation interference with other electronic equipment. The amplifier output will eventually be fed into an inductive load that absorbs almost no energy. By using a (class D) switching amplifier design, and by proper design of the low-pass filter, the total power consumption of the amplifier unit can be minimized, reducing the demands for circuit cooling and for power supply capacity. The low-pass filter 37 would likely be a passive one, and would not introduce substantial phase-shifts to the voltage waveform at the frequency used. The signal picked up by the serially-connected loops, which in one embodiment are wrapped around a patient as shown and described below in relation to FIG. 6, is first fed into band pass filter 44. The purpose of this filter is to increase the system noise immunity. The filter can be designed as a narrow-band resonant transformer, effectively implementing galvanic separation of the conductive wires close to the patient and the rest of the apparatus.

Pre-amplifier 48 is useful since the noise performance of the amplifiers is better than that of demodulator 53. The gain of the amplifier need not be more than necessary to suppress the noise of the demodulator, with a typical value of about 20 to 25 dB.

The coherent demodulator 53 rectifies the alternating voltage signal, and is easily implemented by CMOS analog switches, such as the CD4016 or CD4066 circuit. Using a coherent demodulator has two advantages. It is very linear over a broad signal intensity range, and together with low-pass filter 58, a substantial improvement in relation to noise suppression is achieved. The effective bandwidth of the amplifier chain will be twice the cut-off frequency of low-pass filter 58, with one example of a typical value of this cut-off frequency being 5 Hz to 15 Hz, with the highest value suited for infants with a higher natural respiration rate.

The signal-conditioning block 63 serves several purposes. It provides amplification of the signal, making it suited for further processing in a computer-based system. Also, the unit provides some means of coarse adjustment of the amplification, preferably controlled by the analyzing software. Since the signal at the output of the low-pass filter 58 contains a substantial DC or constant component (corresponding to the total volume of the body inside the coils), some means of subtracting this component will increase the sensitivity of the system in detecting small volume changes. Such subtraction can be made with an electronic high-pass filter, the cut-off frequency of which must be substantially below common respiration frequencies (0.05 Hz or below). In order to shorten the time for the output signal to stabilize at start-up of the system, a means of shortening the time constant of this filter (by resistor switching) is desired. In some cases, where slow changes not related to respiration are measured, absolute readouts of volume without any zero subtraction might be desired. Applications of this might be monitoring of edema development, vascular volume reflexes, muscle growth or atrophy, effects of surgical procedures, etc.

Figure 14:
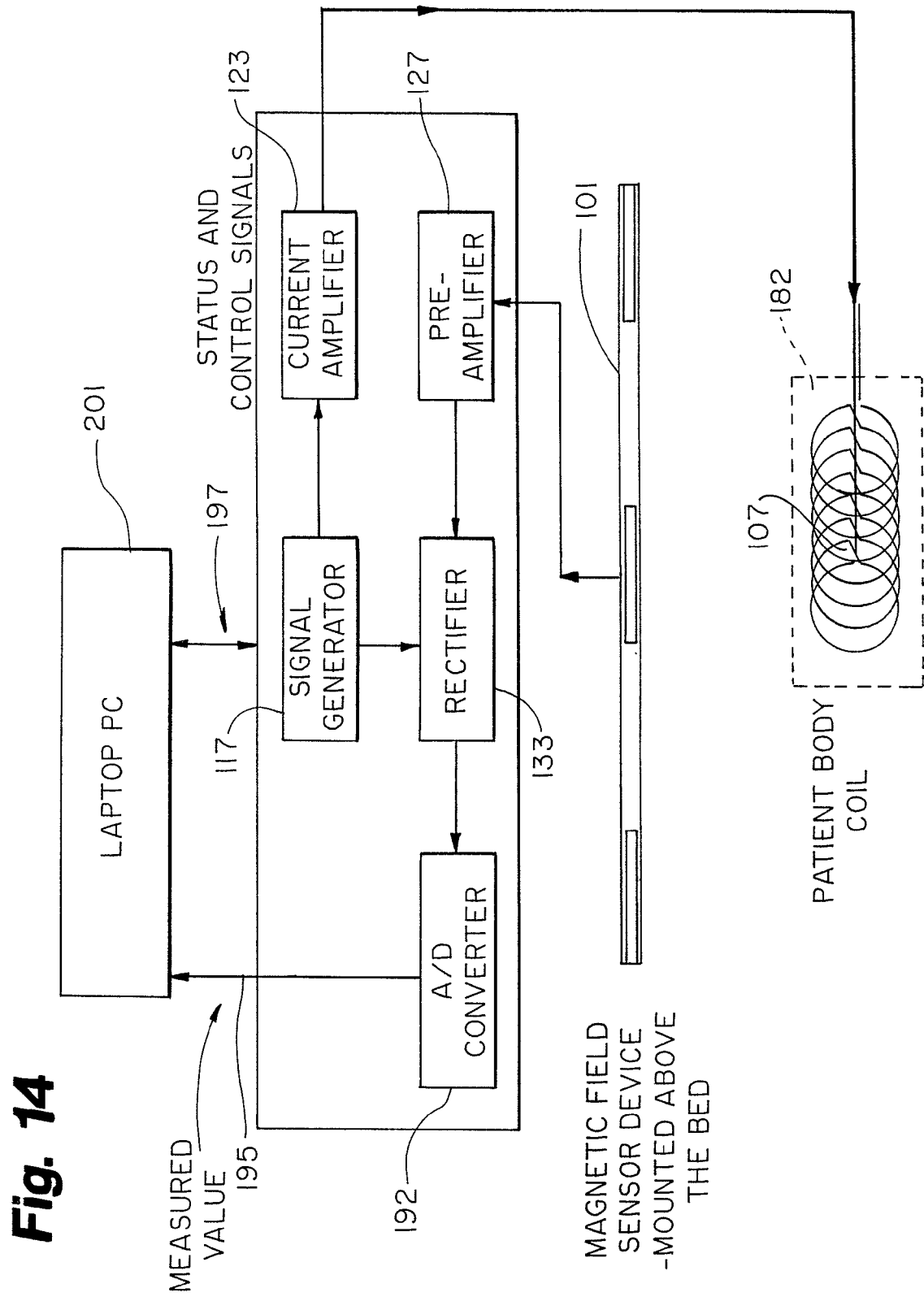
FIG. 14 is a block diagram schematic view of one embodiment of the system of the invention.

The electronic circuits described above are easily constructed within less than 50 cm$^2$ of circuit board area, and could be integrated with an A/D converter and interface control circuitry on a plug-in board for an ordinary personal computer, for example as shown in FIG. 14 below. A complete stand-alone unit could also be made, with the size and complexity being dependent on the amount of signal analysis, presentation capability and storage capacity built into the unit. It should be emphasized that the above illustrative description is for only one embodiment of the invention, with numerous alternate means of practicing the underlying technology also being within the scope of the appended claims. Parts of the function of the suggested block diagram in FIG. 2 could be implemented using digital signal processing or other means. At least one alternate construction is to let all processing of the received signal be digital from and including demodulator 53 with a sampling rate of exactly twice the loop current frequency.

The transducers containing the current loops can be made with varying materials, such as copper or similarly conductive metalization, as well as other designs. For example, one design of elastic electrical conductors might integrate a spring component with the electrical conductor. Also, ease and costs of manufacturing are important. Another solution is to develop a disposable unit, based on metallized plastic bands as the conductor elements. Since the induced voltages are very low (in the order of a few millivolts), and the impedances are low (unless the number of loops becomes high), there may be no need to use insulated conductors. Indeed, the magnetic field generated by a room coil is weaker than that generated by the deflection magnets in a television set. Prolonged exposure to such fields is generally deemed to be harmless. Since a pick-up conductor coil wrapped around the patient can be galvanically separated from the rest of the equipment (as is already done in most other electrical equipment used for patient monitoring), there will not be any electrical shock hazards either.

Figure 3:
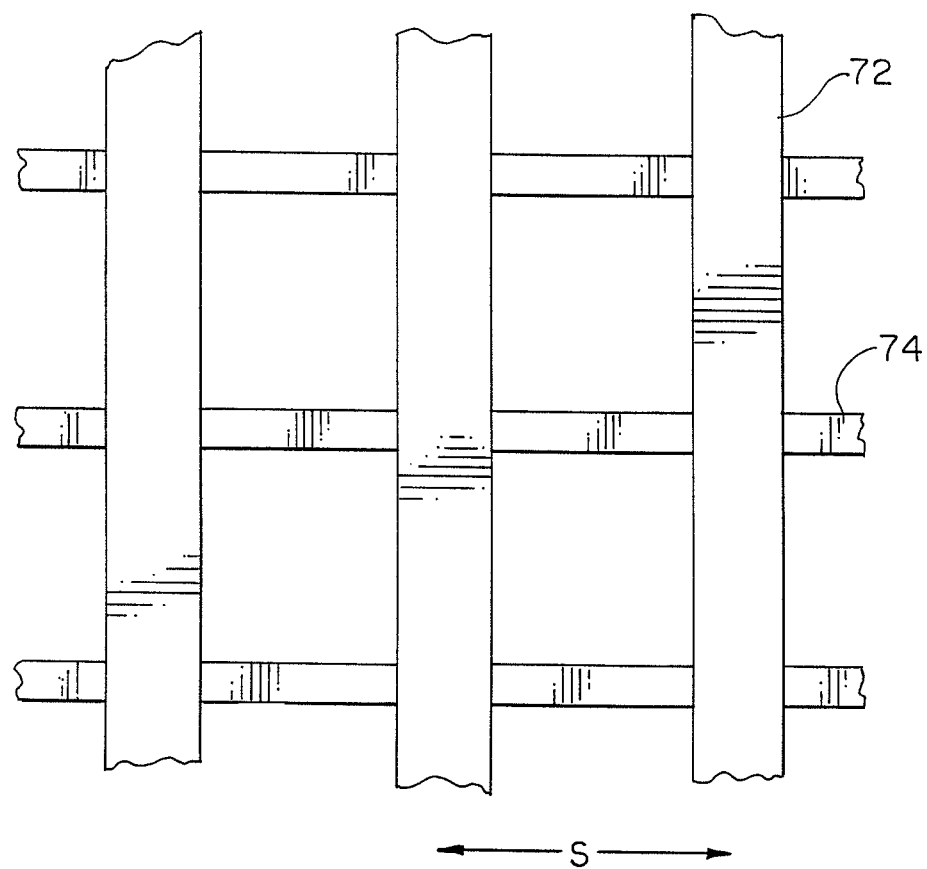
FIG. 3 is one embodiment of a transducer design for use as a coil means.

One embodiment for the design of a disposable transducer is shown in FIG. 3. Strips of metallized foils 72 and plain plastic foils 74, possibly one cm wide, are made into a meshwork by welding at the cross sections. Alternatively, the whole assembly can be stamped from a sheet of foil with metallized bands on it. The thickness of the foil is selected so that the zig-zagged strips have a suitable elasticity. A rectangular sheet of such meshwork is wrapped around the patient or I subject, with a skew, so that the conductor strips are turned into a helix. The seam must provide electrical conducting, either by using some sort of clips, or simply by twisting the pairs of strips together. A cable may be connected to the recording apparatus. It is recognized that other devices may be used to arrange the coil configurations around the object to be measured, for example, as will be discussed below.

Figure 2:
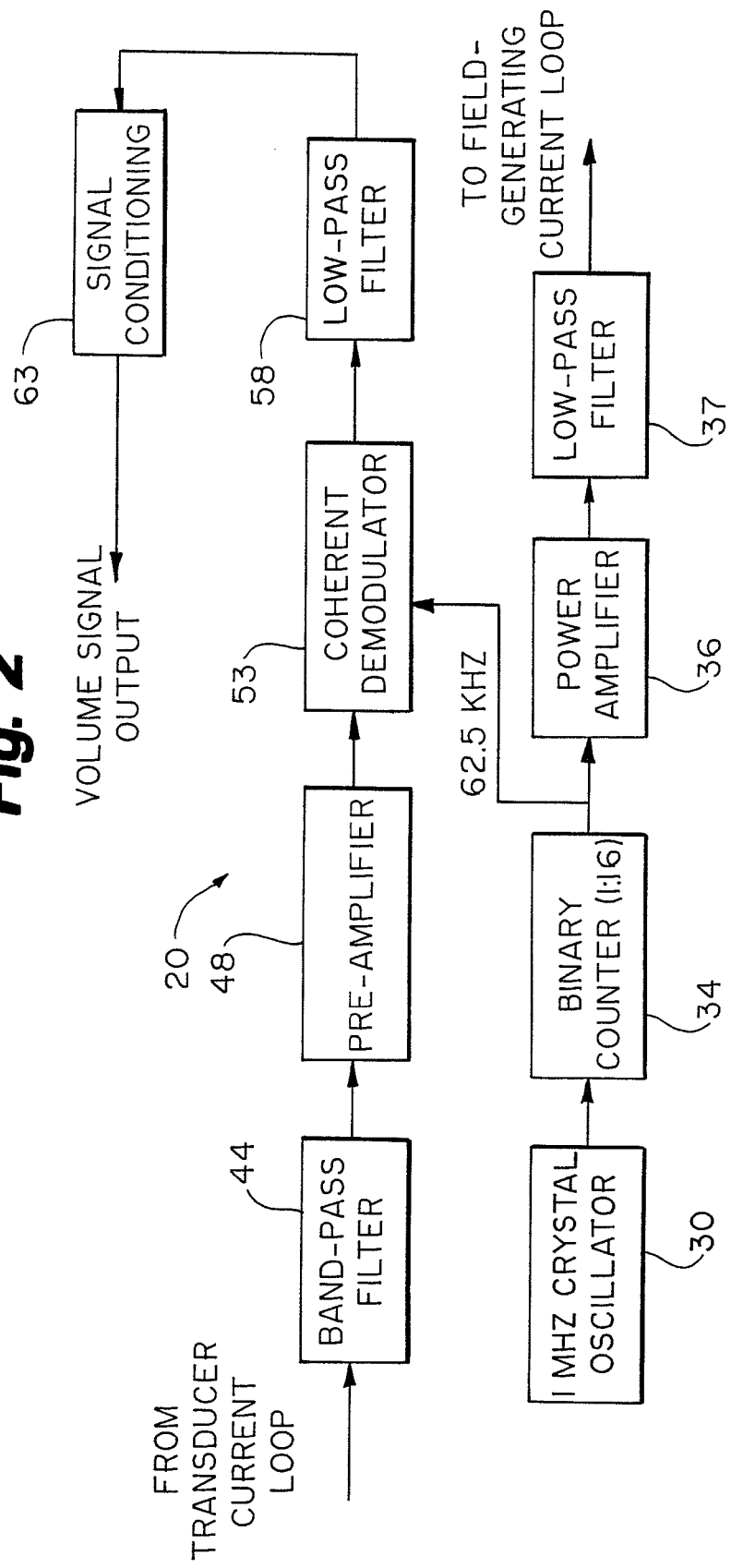
FIG. 2 is a block diagram of a first embodiment of the system of the invention.

One embodiment of the system according to FIG. 2, with some minor modification, was tested using the following parameters:

Current frequency: 70 KHz
Loop current: 200 mA (a 4-turn loop was used, thus the effective current was 800 mA)
Loop size: 2×2 meters
Magnetic field strength in patient body: ≈2 µT
Incremental volume sensitivity (system noise level): 1 ml This embodiment deviates somewhat from the suggested diagram in FIG. 2. A free-running RC-oscillator was used as the frequency control element, and the low-pass filter between the power amplifier and the room loop was omitted. More strict conformance with the block diagram in FIG. 2 will probably result in even better performance, especially with regard to the noise level.

A sample recording from the use of this embodiment is shown in FIG. 4. The volume waveform 81 can be used to calculate breath-by-breath tidal volumes in liters 77 by considering the amplitude of the waveform. Ventilation in liters per second 75 can be found by dividing the tidal volume by the duration of the individual cycle. The instantaneous frequency of respiration (not display) can be found by inverting the duration of the cycles. By careful inspection, variations are observed in the volume that occur in synchrony with the heart rate, and which probably reflect variations in thoracic and abdominal blood volume caused by the beating action of the heart. A magnified view of the raw volume curve 81 in FIG. 4 (from 61 to 64 seconds on the time axis) is shown in FIG. 5 to demonstrate cardiac pulsations in volume. These pulsations are, however, far smaller than the expected cardiac stroke volume of the subject, and reflect the net volume variations of summed abdominal and thoracic blood volume, which might be related to the fraction of the cardiac stroke volume that is diverted to the limbs and brain. Clearly, this provides a valuable diagnostic indication by analysis of this waveform, which may be used for monitoring and assessment of patients with heart failure, shunts or valvular disease. The waveform can easily be extracted from the underlying respiratory variations by coherent averaging, possibly using the patient's ECG as a timing reference. Volume minima coinciding with cardiac end-systole are indicated with arrow markers $C_{es}$. Thus, an apparatus combining respiratory and cardiac monitoring is disclosed. The curve trace of FIG. 5 also demonstrates the noise level of the system which, when translated to measured volume, is in the order of one ml RMS or standard deviation.

As noted above, a typical use of the invention is to continuously measure the volume or area of the chest and abdomen of a human patient. This volume or area will show variations in synchrony with the movements of breathing. These variations correspond to the changes in the volume of gas contained in the lungs, since all fluids and tissues present in the measured volume are incompressible. It is essential also to include the abdomen in the measurement, since breathing action also comprises up and down contraction of the diaphragm muscle, which again causes inward and outward motion of the abdominal walls. Analysis of the time course of volume variations may be used for estimating the quantitative amount of breathing, and a plurality of variables describing the breathing pattern, such as frequency, depth of breath (tidal volume) and airway flow are also discernible.

It should be noted that this invention occurred due to the recognition of the shortcomings of the previously known technology for measuring volumes and areas of objects having an outer material within which an inner volume may change. In addition to human torso and limbs, this invention is well suited for use in the industrial applications of various types, such as where internal volumes may be fuel containers, propellants, or other materials having variable volumes or areas. Regardless of the application, the inventors have recognized the value of the fact that the induced voltage in a conductor loop by a homogeneous alternating magnetic field is exactly proportional to the loop area, independent of the loop shape. The induced voltage in such loops will be added together when the loops are connected in series, for example as when the voltages from individual battery cells are added in everyday electrical equipment. This provides the basis for the measurements of volumes by a single voltage reading from a stack of loops with equidistant spacings.

In addition to greater accuracy of this system and method of obtaining measurements, this technique is also important due to its speed. In particular, the system of the invention does not need to be calibrated to each patient. Rather, volume and area measurements may be accurately taken regardless of the shape or variation pattern of the object/patient provided that the conductive coil follows the contours of the object's/patient's surface contours. For example, in one embodiment, a patient may be equipped with a tightly fitting elastic shirt or garment. This shirt has embedded electrical conductors that comprise a plurality of closed circumferential loops that closely follow the body contours. Electromagnetic induction between this body coil and another remotely located fixed coil is then measured. This may be done by feeding an alternating electrical current (with frequency in the range of about 10 kHz-200 kHz) through either coil, and measuring the induced voltage in the other coil. It is important to note that magnetic fields that are used in the invention are not affected or modified by the presence of body tissue, so the physical laws describing electromagnetic phenomena in void spaces are still valid.

Figure 7:
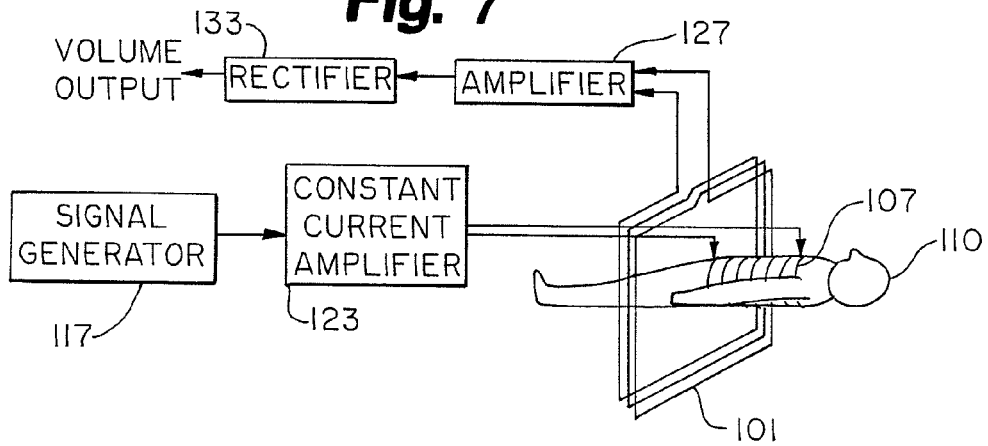
FIG. 7 is a schematic view of a third embodiment of the invention.
Figure 8:
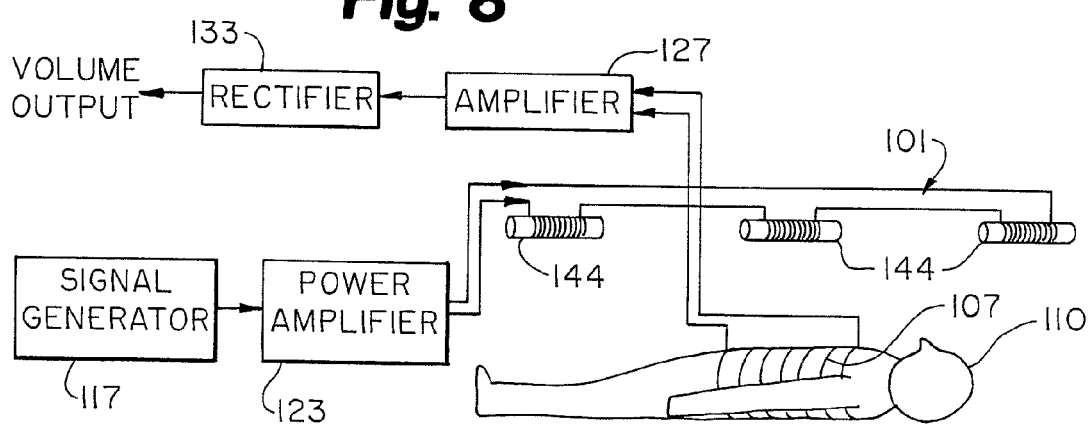
FIG. 8 is a schematic view of a fourth embodiment of the invention.

In one embodiment of the invention, a passive use of the patient coil is used, for example as will be later discussed in relation to FIG. 6. In that embodiment the room coil 101 is generating the magnetic field rather than in a "reversed" arrangement where the patient coil is energized instead of the remote or room coil. Such a reversed arrangement will be further described below in relation to FIG. 7. The first embodiment mentioned above comprised a large (a few meters or more) electrical conductor loop mounted along a building structure such as a wall, floor, or ceiling in order not to be obstructive. However, another embodiment of this coil is possible and consists of a plurality, such as three, carefully positioned and matched small coils, as shown in FIG. 8. These coils will together generate the same type of magnetic field as a large coil would do at the patient measurement site. These embodiments for coil assemblies can be used instead of a bulkier room coil either as a magnetic field generator, or as a magnetic field sensor in the reversed coil arrangement. When the design of the overall system uses this coil configuration as a sensor, it may be possible to use non-inductive technology, such as point sensors or magnetometers, or the like. In the embodiment of FIG. 7, instead of generating the magnetic field with the room coil, the patient coil is energized and used for generating a magnetic field whose properties depend on the volume or area to be measured; while the room coil or three-coil assembly mentioned above is used for picking up an induced voltage caused by the field. By proper design of the electronic circuits that energize the patient coil (constant current amplifiers), the desired linear area or volume dependency of the induced voltage will be preserved.

Figure 10:
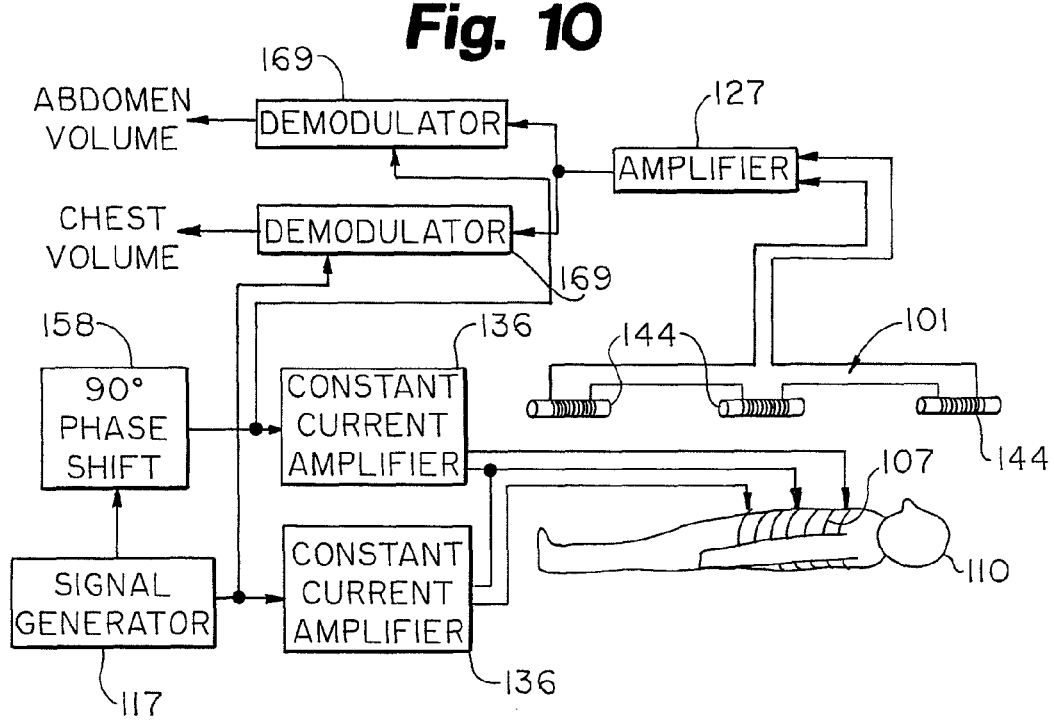
FIG. 10 is a schematic view of a sixth embodiment of the invention.

Another refinement of the system allows simultaneous measurement of two portions of an object, such as a plurality of patient volume compartments, typically the chest and abdomen. This gives supplementary information about the distribution of muscular effort in breathing, and provides information relevant for diagnosis of infant pulmonary diseases, especially diseases associated with airways obstruction. Adding the two measured volumes will still give the total volume measurement advantages of the other embodiments. In order to perform simultaneous measurements, the patient coil is divided in two halves by an electrical "tap" connection at the center turn, as shown in FIG. 10.

Thus what has been provided by this invention is measurement of the area of an electrical conductor loop by recording of the induced voltage in the loop when the loop is positioned in a homogeneous magnetic field. The magnetic field must be alternating, such as a field generated by an alternating electrical current. The area of the loop is, according to physical laws, proportional to the induced voltage. Also, the invention enables measurement of the sum of areas of multiple conductor loops by recording the induced voltage either individually, or as a single measurement when they are electrically connected in series. Measurement of the amount of volume contained inside a plurality of equidistantly stacked conductor loops, by measuring their summed area and multiplying this measured area with the distance between the loops to obtain volume, is also disclosed. The use of these techniques to measure cross sectional areas or volumes of parts of animal or human bodies, using a system of one or more elastic and compliant conductor loops tightly wrapped around the body part, is quite advantageous. Further benefits are taught by the systems and methods herein for achieving accurate measurements of variations in the volume of an animal or human body with the above techniques in order to record breathing, and measurements of variations in the volume of an animal or human body with the above techniques in order to record volume variations caused by cardiac activity. Additional embodiments of the invention are disclosed which provide the further advantages of reversal of electrical coil connections; more compact design for the room coil, comprising two or more smaller coils with optimized shapes and positions; an arrangement comprising three small rod-like coils wound on ferrite cores arranged along a straight line, with optimized positions and signal intensity weighting to generate a homogeneous magnetic field or sensing volume encompassing the patients body or body parts; and simultaneous measurement of two or more areas or volumes by phase, frequency or time multiplexing, using any of the techniques above.

The inventors have determined that implementation of the following embodiments require adherence to several principles. First, the electrical conductor coils that are wrapped around the body part or object to be measured must follow the body/object surface contours, even when these contours change shape. Thus the coil assembly must be elastic and deformable. Second, for measurements of volume, the coils that are wrapped around the body/object part must be stacked with a known spacing between each loop. Coil loops stacked with a constant spacing might be connected in series electrically in order to sum up their voltages and thus to ease volume calculations. Third, the remote coil or coils must, when energized by an electrical current, generate a magnetic field that is reasonably homogeneous (of equal magnetic field strength) at the location of the body part to be measured. Only the vector component of the magnetic field that is perpendicular to the coils that are wrapped around the body needs to be considered regarding this homogeneity. It is further desirable that the remote coils must be able to record the field from a point-sized magnetic dipole located inside the volume to be measured (i.e. the patients body) with a sensitivity that is independent of the location of the dipole, as long as the dipole is oriented perpendicular to the patient body coil loops. It is further desirable to use the remote coil or coils to generate a magnetic field (by feeding an alternating electrical current through them), and then recording the induced electrical voltages in the coils wrapped around the body part to be measured. The voltage will be proportional to the area or volume enclosed by the coils. The remote coil or coils might be arranged in a manner that meets the homogeneity criterion noted above. Finally, it is desirable to feed an alternating current through the stacked coils wrapped around the body part to be measured and then to measure the magnetic field generated by this current. This can be done by recording the induced voltages in the remotely located coil or coils. The voltage will be accurately proportional to the area or volume enclosed by the patient body coils. During these measurements it is essential to keep the current in the patient coil constant even if the self-inductance of this coil varies due to dynamic variations in shape. Thus, a constant-current circuit, or equivalent means, must be used for energizing the patient coil. The design of such a circuit is trivial for those skilled in the art.

Several embodiments of the system and methods of the invention are disclosed in FIGS. 6-11. In FIG. 6, an arrangement is shown in which a conductive coil means 107 is configured tightly about the various circumferences of a torso portion of a human 110. Fixed coil means is remotely located relative to the conductive coil means about the human. Current, generating means is provided and generally shown as signal generator 117 and power amplifier 123 to create an induced voltage in the conductive coil means which changes over time due to the respiration of the human 110. The induced voltage in the conductive coil means is then amplified by amplifier means 127, and rectified by rectifier means 133, and provided as a volume output that is used for measurement of area or volume. The system and method embodiment of FIG. 7 is similar to those of FIG. 6 except that in FIG. 7 the conductive coil means 107 is energized by a constant current, and the induced voltage in the fixed coil means or room coil is used for measurement of area or volume. As noted above, a constant current amplifier means 136, or equivalent circuit component, is provided in this embodiment.

Figure 9:
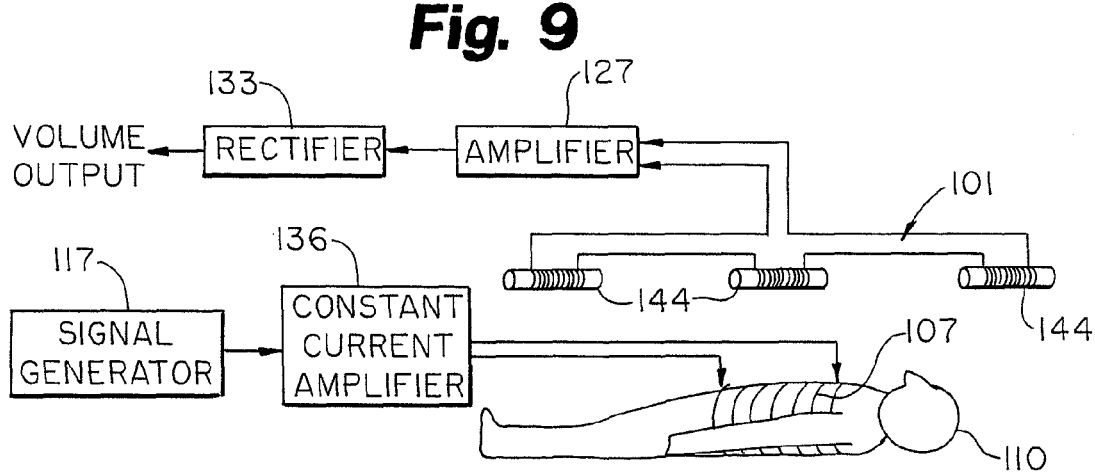
FIG. 9 is a schematic view of a fifth embodiment of the invention.

FIGS. 8 and 9 illustrate the use of a more compact three-coil system design for the fixed coil means instead of the large room coil configuration of earlier embodiments. The individual coils 144 might be serially connected as shown in FIGS. 8 and 9, or they might also be connected in parallel if this is considered during their design. Alternatively, magnetic field sensing devices not based on electromagnetic induction could be used, such as sensors based on the well known Hall effect. Arrangement of a plurality of small coils above the object being measured is designed to generate a homogeneous magnetic field. The coils are typically wound on ferrite rod cores and each coil will then generate a magnetic field pattern similar to that of a magnetic dipole. The positions and number of turns of the coil loops are optimized to satisfy the homogeneity criterion noted above. The serial connection assures identical currents in all three coils. The individual field strength contributions of the coils might be set by their number of loops, physical dimensions or magnetic core material permeability. One example of a three-coil system includes a small cylindrical coil, having about a 10 cm length and 1 cm in diameter. This will generate a magnetic field that closely resembles that of two opposite magnetic monopoles at the two coil ends. The field can be strengthened substantially by inserting a rod made of a material with high magnetic permeability into the coil. A suitable material is ferrite, which is similar to the core material in electronic high-frequency transformers. The remote magnetic field from such a device is close to that of an ideal magnetic dipole, which can be described in exact mathematical terms. The process of finding an optimized design for a homogeneous field is initiated by deciding a set of physical constraints, such as the desired shape and extension of the spatial volume where a homogeneous field is desired, and the space into which a given number of such coils are to be positioned. A set of parameters or degrees of freedom must also be defined, with typical parameters being coordinates for the position and angular orientation of the individual coils, and the strength of the field generated by the individual coils. A general numeric error minimalization routine such as the Levenberg-Marquard method is then used to adjust the parameters to find a solution to the problem where the field homogeneity is maximized. The three-coil design described herein has been developed with this method.

Systems according to these embodiments also comprise sensing and control means for controlling operation of the system. Timing and multiplex switching means may also be included for providing simultaneous measurement capabilities of multiple portions of the object being measured, for example a thoracic region and an abdominal region, or perhaps a plurality of limbs. One of the methods of performing a plurality of simultaneous volume or area measurements is to use phase encoding of the signals. The scheme can be adapted to systems where the patient coil is energized, and the room coil is used for sensing the field, as shown in FIG. 10. The two constant current amplifiers 136 are driven by signals that are phase shifted 90° at phase shift means 158 with respect to each other. The patient coil or conductive coil means 107 is equipped with a center-tap connection means, so that the two halves can be energized by independent currents. The two demodulators 169 rectify the signal that has been picked up by the three room coils 144 and amplified. Since the demodulators receive reference signals that are phase-shifted in the same manner as the inputs to the current amplifiers, they will respond to signal components that match the phase of the two patient coil signals. The apparent swap of output signals (the demodulator that receives the same phase as the abdomen coil current gives an output that reflects chest volume) is caused by an inherent 90° phase shift of the induced voltage in the sensing room coils compared to the current-dependent magnetic field strength from the patient coils. It is recognized that various techniques might be used to perform simultaneous measurements of two or more volumes or areas. If the room coil generates the magnetic field, then independent signal processing chains consisting of amplifiers and rectifiers as shown in other figures can be connected to any number of coils wrapped around the patient's body. For the coil arrangement indicated in FIG. 10, the different patient coils 107 might be driven with currents of different frequencies, and electronic band-pass filters might be used to extract the individual volume signals from a common room coil and preamplifier. Time multiplexing might also be used, energizing the patient coils in a rapidly repeating sequence, typically cycling through all coils between 10 and 1000 times per second, and sampling a common volume output signal in synchrony with this sequence to separate the volume measurements from each other. An additional potentially useful technique for simultaneous measurements of several volumes might be to use different, non-correlated pseudo-random bit sequences for generating patterns of current variation in two or more patient coils. The voltage picked up by the room coil is amplified, and the individual volume signals are recovered by demodulating the composite signal using the corresponding bit sequences as reference signals. Due to the encrypted nature of pseudo-random bit sequences, this type of instrument is expected to be very immune against electromagnetic interference noise, and instruments located close to each other will not interfere with each other's operation.

A measurement system as described above, with any of the disclosed room coil designs or electrical connection arrangements needs to be initially calibrated but not calibrated at every patient or object measurement session. This calibration will compensate for variations in: the current used for generating the magnetic field, the exact geometrical arrangement of the room coil with respect to the patient's position, and the gain of the electronic amplifier and characteristics of the rectifier circuit calibration is performed by connecting a reference coil instead of the patient coil, and positioning this reference coil in the same position as the patient's body will be later during measurements. The summed cross-sectional area of the loops of the reference coil are known from the geometry and number of turns of this coil. Typically, this area should be of the same order of magnitude as the area of the patient coil. A constant, $k_c$ is then calculated as:

$$k_c = a_c/U_c \qquad \text{Eq. 3}$$

where $a_c$ is the area of the reference coil, and $U_c$ is the voltage reading of the volume output signal.

For measurements of area, using a single conductor loop wrapped around the relevant body part, the area A can be calculated as:

$$A = U_c \cdot k_c \text{—where } U \text{ is the measured voltage.} \qquad \text{Eq. 4}$$

During volume measurements, using serially connected equidistantly spaced loops the instantaneous volume V is calculated from the voltage reading U as:

$$V = U \cdot d \cdot k_c \text{—where } d \text{ is the spacing between the loops of the patient coil.} \qquad \text{Eq. 5}$$

Example 1

A circular electrical conductor loop with a radius of 1.5 meters was placed on the floor. An alternating current of 0.1 A with a frequency of 100 kHz was fed through the conductor from a signal generator. A small, 10×10 cm (100 cm²) square conductor loop was connected to the input of a broadband signal amplifier with a gain of 40 dB, and the output from this amplifier was passed through a narrow 100 kHz band-pass filter with no gain. The output signal from the filter was presented on an oscilloscope screen, where voltages could be read by cursors. When the small loop was positioned flat on the floor in the center of the larger current loop, a voltage of 5 mV p/p was measured. This voltage remained essentially constant when the small loop was elevated 50 cm above the floor, and it also remained constant when the small loop was moved up to 50 cm in any horizontal direction away from the center of the large current loop. Another square loop, measuring 14.1×14.1 cm, with an area of 200 cm² was then connected instead of the 10×10 cm loop. The voltage reading was now 10 mV.

Example 2

The same conductor loops as described in Example 1 were used, but the 0.1 A current from the signal generator was fed to the 100 cm² loop, and the large loop on the floor was connected to the input of the 40 dB broadband amplifier. The small loop was positioned as explained in Example 1. The same general relations between induced voltage and loop position and area was observed as in Example 1, however the voltages were reduced to 250 µV when using the 100 cm² loop, and 500 µV when using the 200 cm² loop.

Example 3

Figure 11:
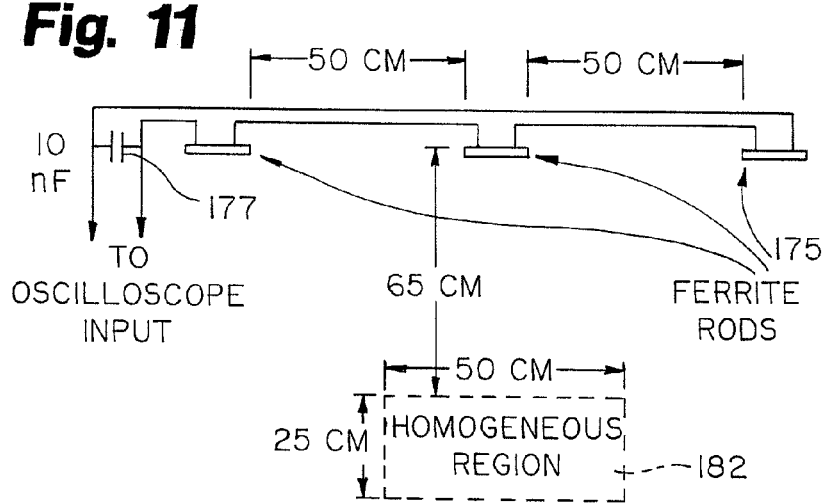
FIG. 11 is a schematic view of a seventh embodiment of the invention.

Referring to FIG. 11, three identical cylindrical ferrite rods 175 with a diameter of 8 mm, length of 150 mm and permeability of 100 were arranged along a straight horizontal line with a common axis. The end-to-end horizontal spacing between each rod was 50 cm. The two outer coils were equipped with 163 turns of lacquer-insulated 0.1 mm copper wire evenly distributed along a central 8 cm segment of the rod, while the center rod had 100 turns arranged in the same manner. The coils were electrically connected in series, and care was taken to assure identical current directions in all coils. The serially connected coils were then tuned to parallel resonance at 100 kHz with a common capacitor 177 of about 10 nF. An oscilloscope directly monitored the signal from the resonant circuit. A 10 cm×10 cm current loop carrying a 100 kHz alternating current of 0.1 A was positioned adjacent to the coil assembly, keeping the orientation of the loop perpendicular to the ferrite rods common axis. It was found that the induced voltage in the ferrite rod circuit varied only 5% from an average value for all positions of the probing coil in the homogeneous region 182 indicated in FIG. 11.

Example 4

The circular room coil described in Example 1 was positioned horizontally 120 cm above the floor. An alternating current of 0.1 A at 100 kHz was fed through the coil from a signal generator. A human was dressed with an elastic Lycra textile shirt that covered the torso from the armpits and down to the ridge of the hip. A helical electrical conductor was attached to the surface of the textile shirt, making a total of 10 equidistant turns around the torso. The spacing between the turns was 5 cm. The conductor was arranged in a fine zigzag pattern to allow for circumferential variations without becoming over-stretched or loosing contact with the body contour. The subject was positioned standing with the chest and abdomen located close to the center of the room coil and the amplitude of the induced voltage in the helical coil was measured to be 350 mV peak to peak with an oscilloscope. Combining this with the reference measurements described in Example 1, the volume of the torso could be calculated as:

$$350 \text{ mV} \cdot 5 \text{ cm} \cdot \frac{100 \text{ cm}^2}{5 \text{ mV}} = 35000 \text{ cm}^3 = 35 \text{ liters}$$

Example 5

The same subject and as in Example 4 wearing the same elastic textile shirt with electrical conductors is used. The subject is positioned supine on a bench, and three small ferrite coils as in Example 3 are mounted 90 cm above the surface where the subject is lying, parallel to the subjects body axis and centered above the subject's chest and abdomen. A constant alternating current of 0.1 A is fed through the coil, which follows the surface contours of the torso. The voltage that is induced in the ferrite coils is measured with an oscilloscope. This voltage is compared to the voltage that is measured when a 100 cm² coil carrying 0.1 A is positioned at the same site as the subject's torso, and a volume very similar to that described in Example 4 is calculated.

Example 6

Figure 12:
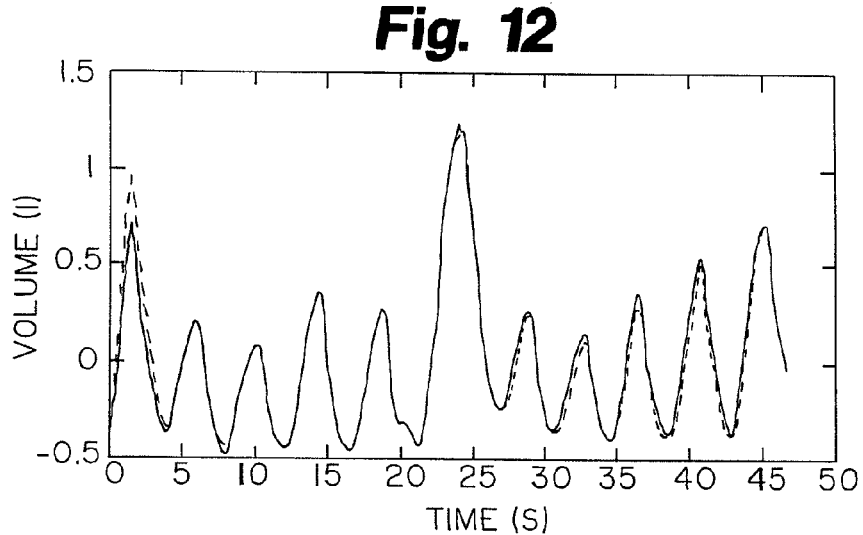
FIG. 12 is a screen view graph of simultaneous recordings using a spirometer and the system of the invention.

The experiment of Example 4 was repeated. The induced voltage from the patient coil was rectified in order to generate a DC voltage signal reflecting instantaneous torso volume. This signal was sampled with 14 bits of resolution by an analog to digital converter, and then transferred to a computer at a sampling rate of 25 Hz. Equation 5 above was used to convert the voltage readings to volume values. The signal was then fed through a digital high-pass filter with a cut-off frequency of 0.05 Hz. This removed the time-averaged volume component from the signal. The filtered signal then reflected breathing activity. The subject's breathing activity was also recorded by connecting the patient airways to a recording dry-seal spirometer by the use of a mouthpiece. A simultaneous recording of breathing by the two methods is displayed in FIG. 12. As shown, the comparison of the simultaneous recordings of breathing volume by a dry-seal spirometer connected to a human subject's airways (broken line), and the measurements using the device described in Example 4 (solid line) are virtually identical. Upward deviations of the traces mean increasing lung air content. To ease the comparison of traces, the spirometer trace has been inverted. The deviation between the traces during the first four seconds is probably related to thermal equilibration within the closed spirometer system.

Example 7

Figure 13:
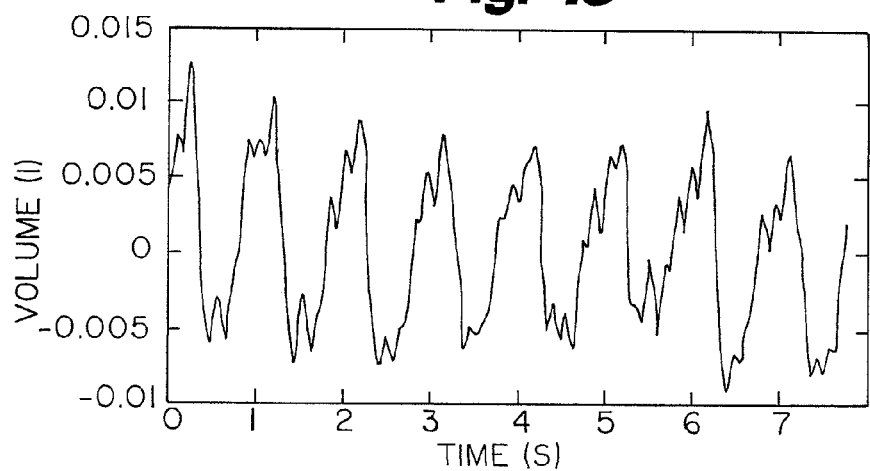
FIG. 13 is a screen view graph of blood volume variations in the chest and abdomen caused by cardiac activity.

The experiment in Example 6 was repeated. Volume measured by the inductive device was recorded for 8 seconds while the subject held his breath in expiration phase. Variations in volume with amplitude of about 15 ml occurring in synchrony with his heartbeats could be seen, as shown in line 188 of FIG. 13. These variations are expected to represent the total blood volume variations in the chest and abdomen caused by the beating action of the heart.

While the above Examples illustrate some of the capabilities of the invention, they are not intended to limit the scope of this disclosure. Also, as referenced above, various system embodiments are contemplated. FIG. 14 discloses yet another embodiment of the measurement systems disclosed herein. Fixed coil means 101 is configured as a sensor for induced voltage created when current is generated in signal generator 117 and current amplifier 123 and fed to conductive coil means 107 within homogeneous region 182. The sensed voltage is amplified at amplifier 127, and is fed through rectifier 133, A/D converter 192, and becomes the measured value 195 that transmits to personal computing and/or display means 201. Finally, status and control means provides signals 197 to give status and control commands.

It is recognized that the functionality and display of the accurate values being measured by the systems and methods disclosed herein present significant advantages to users of the invention. The speed and accuracy greatly enhances the value of multiple, real-time traces, traces with rapid x-axis and waveform details, traces with a wide range of time axis span of minutes to hours, and reconstruction displays. Numerous other display features and diagnostics are enabled due to the system advantages identified above.

Additional solutions to this and related prior technical approaches relate to noise immunity of the system. These solutions improve the signal to noise ratio and significantly enable measurements of even small variations in tidal volumes, even in neonates down to less than 1000 g. The improvements relate to the arrangement of the fixed magnetic coils with the potential ability for generating a homogeneous magnetic field in the spatial volume occupied by the patient's body part, which is the volume for which measurements are desired. Again, this disclosure describes at least two main classes of coil arrangements. The first is one or more fixed coils which are energized with an electrical current to generate a homogeneous magnetic field, and wherein the coil wrapped elastically around the patient's body (i.e. the patient coil) is used as the volume sensing element. The second arrangement is one in which the patient coil is energized from a constant current source, and a fixed coil arrangement with homogeneous field properties is used as the volume sensing element. The further improvement and solution relates to the design of the fixed coils and is beneficial to both types or arrangements of measurement systems described above.

One embodiment of a working prototype instrument is based on the second arrangement noted above, relating to energizing the patient coil. In this embodiment, the system overall performance was reduced due to unwanted reception of stray magnetic field components from remote sources, such as computer power supplies, CRT screens, power lines and other electrical appliances. This again caused noise and uncertainties in the values of the measured volumes. The problem was related to the properties of the fixed coils, with three individual coil elements arranged along a straight line as described herein above, for example, in relation to FIGS. 8-11 and 14. A remote source of a magnetic field will generate signals with the same phase in the three coils since they are aligned in the same spatial direction, and their induced voltages are summed. This will result in a significant source of unwanted noise, the mitigation of which is the focus of this further solution.

Figure 15:
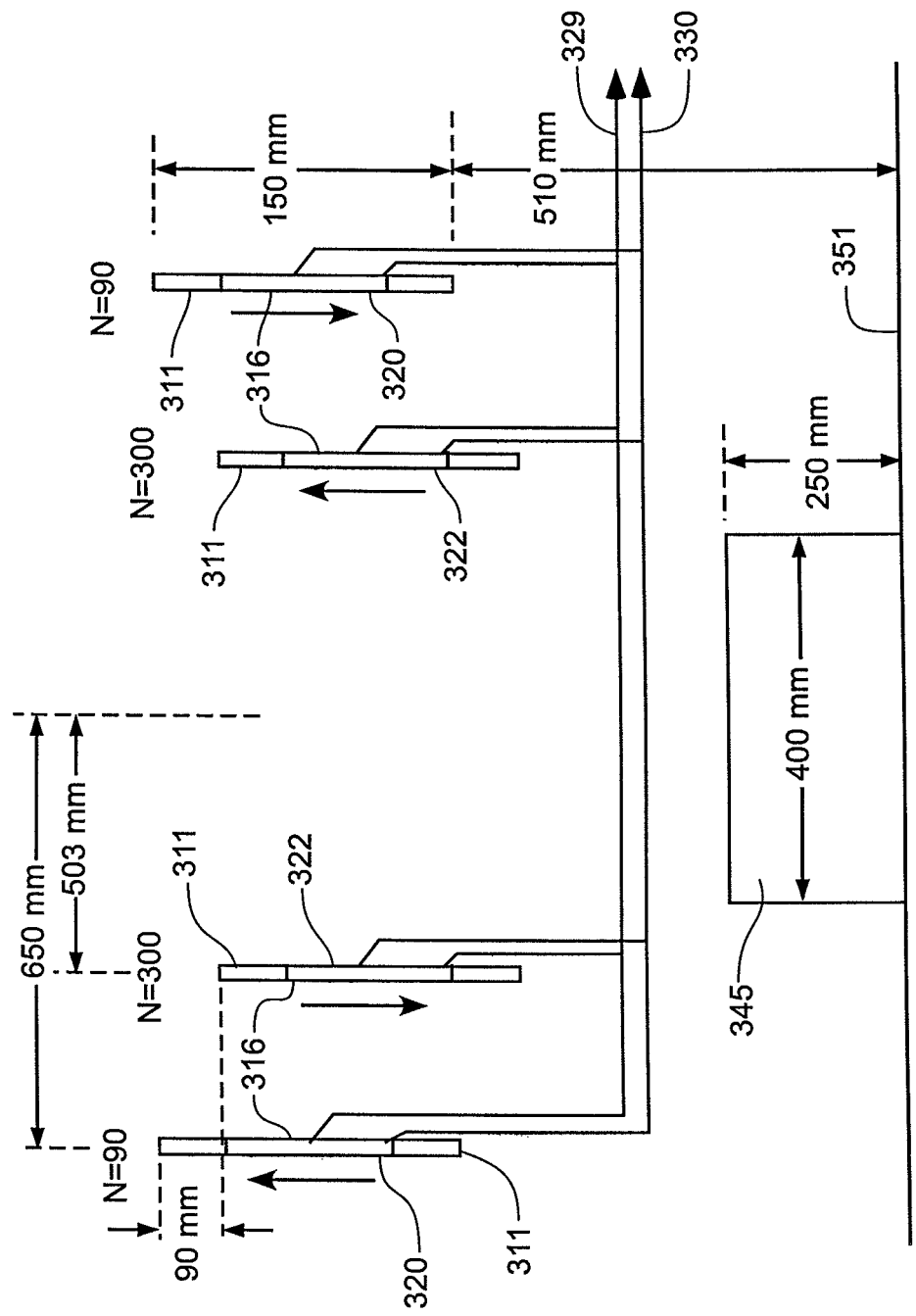
FIG. 15 is a schematic view of an embodiment of the invention.

This recognition led to arranging the fixed coils so that the homogeneous field properties in the volume occupied by the patient's body is conserved, while magnetic noise signals from remote sources are prevented from reaching the measurement apparatus. This has been achieved by using an even number of pair-wise matched identical coils, connected electrically in opposite phases, so that the signals from remote sources (having the same intensity in both coils of the pair) will be cancelled. One embodiment of such a system 300 configuration is shown in FIG. 15. In this embodiment, ferrite rods 311 are configured with 8 mm diameters, 150 mm lengths, and a μ value of 100. Rods 311 each have lacquer insulated copper wire, shown at portions 316, and having the number of turns as specified by 320=90 turns and 322=300 turns. This arrangement of four ferrite rods has the spacing as also indicated in FIG. 15, with electrical connections 329, 330 also shown. This fixed coil configuration is in relation to the spatial region 345 (or volume) having homogeneous sensitivity (or at least near-homogeneous signal sensitivity), arranged on mattress or similar surface 351.

This further embodiment of a technical solution for removing unwanted noise from reaching the measurement system is based on the assumption that the unwanted noise is caused by a magnetic field that has a uniform intensity in the spatial region occupied by the fixed coils. It is understood that any combination of coil orientations and coil turn numbers (determining the signal sensitivity for each coil) that bring the sum of signals from a magnetic field of uniform intensity to zero will work, and that using matched pairs of coils to acquire this property is one out of several ways to bring the overall signal from remote magnetic sources down to zero. In principle, therefore, and relating to all possible arrangements of coils to achieve such principle, it might be stated that the improved configuration should result in total magnetic moment of the fixed coil assembly being zero.

The added requirement that the coil system must be able to generate a relatively homogeneous magnetic field in the spatial region occupied by the patient body does, however, likely limit the range of available designs. Although this principle has been evaluated and is achieved with the designs mentioned in the examples below, this further inventive solution should not be limited to these particular designs, but rather it should preferably cover all arrangements of magnetic sensor elements that have the combined properties of a relatively homogeneous spatial sensitivity in the space where the patient's body part is located; and a sum of received signals of zero when all coils are exposed to a uniform magnetic field.

The fixed coil arrangement with the properties outlined above might also be used as a source of the measurement magnetic field, in an instrument as described in the first arrangement noted above. The advantage of the new fixed coil design will then be that the magnetic field that is generated rapidly decays with increasing distance from the instrument, thus reducing potential interference with other electronic instruments, including other related measurement systems located in the same room or building.

Example 8

A volume measurement system was constructed according to specification above and using the second coil arrangement, i.e., energizing the patient coil, using a fixed coil design comprising 3 coils in a row above the patient's bed. An elastic patient coil having 12 turns spaced 2 cm apart was applied to a cylindrical phantom body of a size comparable to a 4 year old infant, and the noise level of the instrument was measured to be about 5 mL rms. The fixed coils were then replaced with coils of the new design as shown in FIG. 15, and the noise level was measured to be about 1 mL rms, corresponding to an improvement of about 14 dB in the overall signal to noise ratio of the system.

Example 9

The experiment described in the previous Example 8 was repeated, and the noise level with the fixed coil design comprising 3 coils in a row above the bed was again measured to be 5 mL rms. Another, identical fixed coil assembly comprising 3 coils in a row was located 4 meters away from the patient coil, in a location where the magnetic field component from the patient coil is expected to be very low. This coil assembly was spatially oriented in anti-parallel with the original fixed coil, i.e., pointing in the opposite direction. The cables from the two remote coil assemblies were then connected via a coaxial T-connector to the input terminal of the measurement instrument, in order for their signals to be summed together. The noise level of the system was now about 2 mL rms, thus an improvement of about 8 dB had been achieved.

It will be understood that various modifications and alternate configurations may be made in the preferred and related embodiments shown and described herein without departure from the scope of the invention, and that the invention embraces all such changes, modifications, and equivalents as are within the scope of the following claims.

What is claimed is:

1. A device for measuring the movement of a patient's body part comprising:
(a) first and second matched pairs of fixed coils;
(b) a patient coil configured to wrap elastically around the patient's body part;
(c) a current source coupled to, and adapted to energize, either the matched pairs of fixed coils or the patient coil; and
(d) a volume sensing element comprising whichever of the matched pairs of fixed coils or the patient coil that is not coupled to the current source;
wherein the first and second matched pairs of fixed coils are arranged (i) to reduce a sum of magnetic noise signals from remote sources to zero when the current source is coupled to, and adapted to energize, the patient coil and the volume sensing element comprises the matched pairs of fixed coils and (ii) to generate a relatively homogeneous magnetic field in a spatial volume occupied by the patient's body part and to reduce potential interference with other electronic instruments when the current source is coupled to, and adapted to energize, the matched pairs of fixed coils and the volume sensing element comprises the patient coil.

2. The device of claim 1, wherein the spatial volume has a center and the first and second matched pairs of fixed coils are arranged symmetrically about a vertical plane extending through the center of the spatial volume and are arranged above a horizontal plane passing through the center of the spatial volume.

3. The device of claim 1, wherein the first matched pair of fixed coils comprise first and second fixed coils connected electrically in opposite phases, and the second matched pair of fixed coils comprise third and fourth fixed coils connected electrically in opposite phases.

4. The device of claim 1, wherein the device is configured to measure variations in tidal volumes in neonates less than 1000 grams.

5. The device of claim 1, wherein (i) the spatial volume has a center, (ii) first and second planes both extend through the center, the first plane being perpendicular to the second plane, and (iii) the first and second matched pairs of fixed coils are arranged symmetrically about the first plane and on the same side of the second plane.

6. A device for measuring the movement of a patient's body part comprising:
(a) first and second matched pairs of fixed coils;
(b) a patient coil configured to wrap elastically around the patient's body part and be positioned in a spatial volume;
(c) a current source coupled to, and adapted to energize, the patient coil; and
(d) a volume sensing element comprising the matched pairs of fixed coils;
wherein the first and second matched pairs of fixed coils are arranged (i) to reduce a sum of magnetic noise signals from remote sources to zero and (ii) such that they would generate a relatively homogeneous magnetic field in the spatial volume if the current source were coupled to, and adapted to energize, the matched pairs of fixed coils and if the volume sensing element comprised the patient coil.

7. The device of claim 6, wherein the spatial volume has a center and the first and second matched pairs of fixed coils are arranged symmetrically about a vertical plane extending through the center of the spatial volume and are arranged above a horizontal plane passing through the center of the spatial volume.

8. The device of claim 7, wherein the first matched pair of fixed coils are each positioned approximately 503 millimeters from the vertical plane.

9. The device of claim 8, wherein the second matched pair of fixed coils are each positioned approximately 650 millimeters from the vertical plane.

10. The device of claim 7, wherein the spatial volume has a bottom and wherein (A) the first matched pair of fixed coils each comprise approximately 300 turns, (B) the second matched pair of fixed coils each comprise approximately 90 turns, (C) the first matched pair of fixed coils are wound on a first pair of rods that are positioned approximately 420 millimeters above the bottom of the spatial volume, (D) the second matched pair of fixed coils are wound on a second pair of rods that are positioned approximately 510 millimeters above the bottom of the spatial volume, (E) the first matched pair of fixed coils are each positioned approximately 503 millimeters from the vertical plane, (F) the second matched pair of fixed coils are each positioned approximately 650 millimeters from the vertical plane, and (G) the spatial volume extends 250 millimeters in the vertical direction and 400 millimeters in the horizontal direction.

11. The device of claim 6, wherein the spatial volume extends 250 millimeters in the vertical direction and 400 millimeters in the horizontal direction.

12. The device of claim 6, wherein the first matched pair of fixed coils each comprise approximately 300 turns and the second matched pair of fixed coils each comprise approximately 90 turns.

13. The device of claim 6, wherein the spatial volume has a bottom and wherein the first matched pair of fixed coils are wound on a first pair of rods that are positioned approximately 420 millimeters above the bottom of the spatial volume.

14. The device of claim 13, wherein the second matched pair of fixed coils are wound on a second pair of rods that are positioned approximately 510 millimeters above the bottom of the spatial volume.

15. The device of claim 6, wherein the first and second matched pairs of fixed coils are wound on first and second pairs of ferrite rods, each rod having a diameter of approximately 8 millimeters, a length of approximately 150 millimeters, and a g value of approximately 100.

16. The device of claim 6, wherein the first matched pair of fixed coils comprise first and second fixed coils connected electrically in opposite phases, and the second matched pair of fixed coils comprise third and fourth fixed coils connected electrically in opposite phases.

17. The device of claim 6, wherein the device is configured to measure variations in tidal volumes in neonates less than 1000 grams.

18. The device of claim 6, wherein (i) the spatial volume has a center, (ii) first and second planes both extend through the center, the first plane being perpendicular to the second plane, and (iii) the first and second matched pairs of fixed coils are arranged symmetrically about the first plane and on the same side of the second plane.

19. A device for measuring the movement of a patient's body part comprising:
   (a) first and second matched pairs of fixed coils;
   (b) a patient coil configured to wrap elastically around the patient's body part and be positioned in a spatial volume;
   (c) a current source coupled to, and adapted to energize, the first and second matched pairs of fixed coils; and
   (d) a volume sensing element comprising the patient coil;
   wherein the first and second matched pairs of fixed coils are arranged (i) to generate a relatively homogeneous magnetic field in the spatial volume and (ii) to reduce potential interference with other electronic instruments.

20. The device of claim 19, wherein the spatial volume has a center and the first and second matched pairs of fixed coils are arranged symmetrically about a vertical plane extending through the center of the spatial volume and are arranged above a horizontal plane passing through the center of the spatial volume.

21. The device of claim 19, wherein the first matched pair of fixed coils comprise first and second fixed coils connected electrically in opposite phases, and the second matched pair of fixed coils comprise third and fourth fixed coils connected electrically in opposite phases.

22. The device of claim 19, wherein the device is configured to measure variations in tidal volumes in neonates less than 1000 grams.

23. The device of claim 19, wherein (i) the spatial volume has a center, (ii) first and second planes both extend through the center, the first plane being perpendicular to the second plane, and (iii) the first and second matched pairs of fixed coils are arranged symmetrically about the first plane and on the same side of the second plane.

24. A method of measuring the movement of a patient's body part comprising:
   (a) arranging first and second matched pairs of fixed coils;
   (b) wrapping a patient coil around the patient's body part;
   (c) positioning the patient coil and the patient's body part in a spatial volume;
   (d) energizing the patient coil;
   (e) sensing a volume of the body part with the matched pairs of fixed coils;
   wherein the first and second matched pairs of fixed coils are arranged (i) to reduce a sum of magnetic noise signals from remote sources to zero and (ii) such that they would generate a relatively homogeneous magnetic field in the spatial volume if the current source were coupled to, and adapted to energize, the matched pairs of fixed coils and if the volume sensing element comprised the patient coil.

25. The method of claim 24, wherein the spatial volume has a center and the first and second matched pairs of fixed coils are arranged symmetrically about a vertical plane extending through the center of the spatial volume and are arranged above a horizontal plane passing through the center of the spatial volume.

26. The method of claim 24, wherein the patient is a neonate less than 1000 grams.

27. The method of claim 24, wherein (i) the spatial volume has a center, (ii) first and second planes both extend through the center, the first plane being perpendicular to the second plane, and (iii) the first and second matched pairs of fixed coils are arranged symmetrically about the first plane and on the same side of the second plane.

28. The method of claim 24, wherein the first matched pair of fixed coils comprises first and second fixed coils connected electrically in opposite phases, and the second matched pair of fixed coils comprises third and fourth fixed coils connected electrically in opposite phases.

* * * * *